United States Patent

Ruppert, Jr. et al.

[11] Patent Number: 5,348,570
[45] Date of Patent: Sep. 20, 1994

[54] AXLE HOUSING BREATHER

[75] Inventors: Malcolm F. Ruppert, Jr., Clarkston; Eric C. Liu, Richmond, both of Mich.

[73] Assignee: Rockwell International Corporation, Pittsburgh, Pa.

[21] Appl. No.: 42,934

[22] Filed: Apr. 5, 1993

[51] Int. Cl.5 .................. B01D 53/22; B01D 19/00; B01D 29/05
[52] U.S. Cl. ............................. 96/6; 96/190; 96/220; 55/502; 55/504
[58] Field of Search .................. 96/4, 6, 187, 189, 190, 96/220; 55/502–504, 507, 509

[56] References Cited

U.S. PATENT DOCUMENTS

| 1,888,150 | 11/1932 | Walker | 55/503 X |
| 1,940,601 | 12/1933 | McCrery et al. | 55/502 X |
| 2,244,395 | 6/1941 | Hill | 55/502 |
| 2,251,964 | 8/1941 | Stackhouse | 55/503 X |
| 2,635,784 | 4/1953 | Bering et al. | 55/502 X |
| 2,732,092 | 1/1956 | Lawrence | 55/502 X |
| 3,557,536 | 1/1971 | Ririe | 55/503 X |
| 3,828,527 | 8/1974 | Briggs et al. | 96/4 |
| 3,909,302 | 9/1975 | Mermelstein | 96/6 X |
| 4,155,247 | 5/1979 | Kaczmarek et al. | 55/502 X |
| 4,171,209 | 10/1979 | Brown | 55/502 X |
| 4,426,213 | 1/1984 | Stavropoulos | 55/502 X |
| 4,445,884 | 5/1984 | Kurtz et al. | 96/6 X |
| 4,853,013 | 8/1989 | Rio et al. | 96/6 |
| 4,863,499 | 9/1989 | Osendorf | 55/502 X |
| 4,886,533 | 12/1989 | Sakashita et al. | 55/502 X |
| 4,957,518 | 9/1990 | Brassell | 96/4 |
| 4,957,522 | 9/1990 | Brassell | 96/4 |
| 5,019,140 | 5/1991 | Bowser et al. | 96/6 |
| 5,108,474 | 4/1992 | Riedy et al. | 55/502 X |

FOREIGN PATENT DOCUMENTS

| 377067 | 7/1990 | European Pat. Off. | 96/4 |
| 3708950 | 9/1988 | Fed. Rep. of Germany | 96/6 |
| 358086 | 9/1931 | United Kingdom | 96/4 |

Primary Examiner—Robert Spitzer

[57] ABSTRACT

A venting mechanism which includes three members. A first member having threads defined thereon connected to a second offering a hexagonally shaped external surface. The third member features a bore which defines an annular surface at the intersection with a bore through the second member. A baffle is located within the bore of the second member by engagement with the annular surface defined between the second and third member. A Gortex film and a wire mesh placed within the bore of the third member are retained by a rolled lip thereof. In this manner, the baffle and the Gortex film act to maintain liquid on one side of the breather while allowing gases to freely pass therethrough.

1 Claim, 1 Drawing Sheet

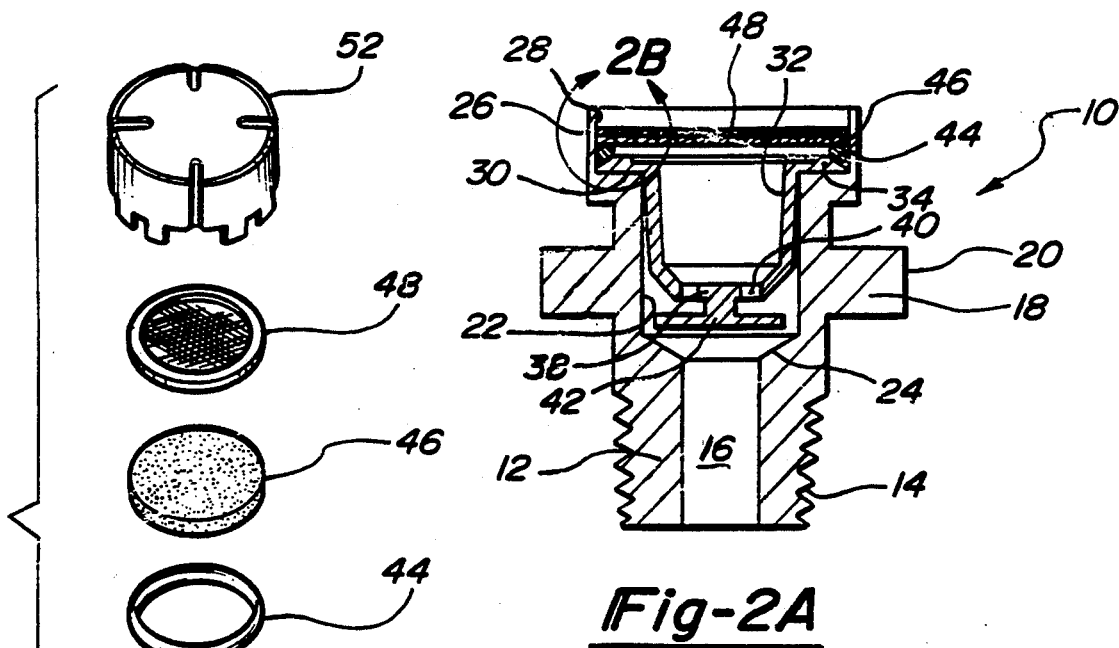
*Fig-2A*
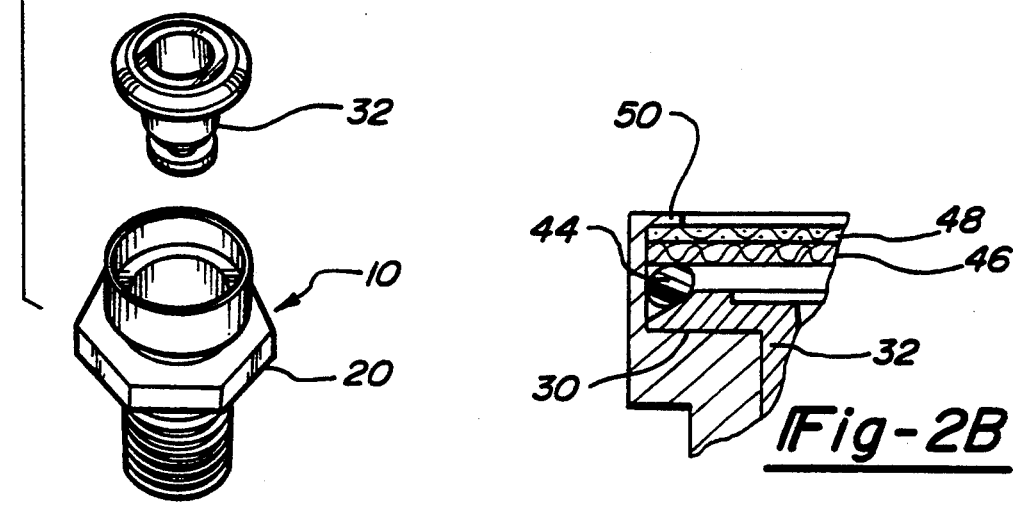
*Fig-1*
*Fig-2B*
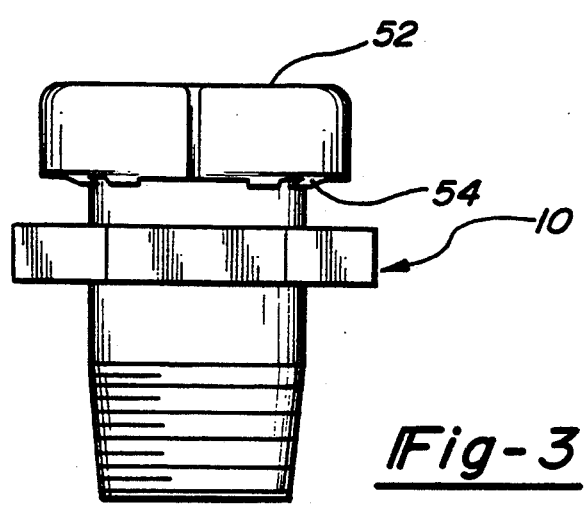
*Fig-3*

AXLE HOUSING BREATHER

BACKGROUND OF THE INVENTION

1. Field of the Invention

This invention relates generally to venting mechanisms and, more specifically, to a venting mechanism which discriminates between gases and liquids.

2. Description of the Related Art

Present venting mechanisms provide a pressure relief avenue between a chamber defined by a housing containing oil bath lubricated gear mechanisms and the atmosphere. During operation of the gear mechanism, air and oil contained within the housing becomes heated causing the air contained within the housing to expand. The resulting pressure within the housing exceeds atmospheric pressure and, therefore, seeks an avenue of relief. Typically, such avenues are in the form of short-pipe extensions with baffle. Air passing through the baffle carries oil which wets the outside of the chamber rendering same tacky and acting to collect atmospheric containments. Over time such a process results in an unsightly condition. The object of the present invention is to provide a breather which discriminates between air and oil preventing the oil from escaping.

SUMMARY OF THE PRESENT INVENTION

The present invention is a venting mechanism which includes an axially extending cylindrical portion which defines three continuously connected members. A first member has a thread defined on the surface thereof and a bore extending therethrough. A second member connected to said first member includes a hexagonally shaped structure defined on the outermost surface and a second bore extending therethrough. The first and second bores intersect to define a first annular surface between the first and second bores. The third member has a third bore defined therein which defines a second annular surface between said second and said third bores. The bore of the second member defines a chamber which includes a baffle placed therein. The baffle has a first radially extending annular portion which is continuously connected with an axially extending cylindrical portion which is continuously connected with an inwardly radially extending portion having at least one opening therein. The inwardly extending radial portion features an axially extending portion connected to a radially extending portion which extends radially proximate the opening defined on the inwardly extending radial portion. The baffle is located within the bore of the second member by engagement of a radially extending annular portion and an annular surface defined between the bore of the second and third member. In addition, the third member includes an O-ring placed in the bore thereof. A Gortex film and a wire mesh placed thereon are maintained within the bore of the third member by a radially inwardly turned lip which at least partially distorts the O-ring and provides retention for the film, the mesh and the O-ring within the bore of the third member. Gortex is a material which offers the properties of permitting gases to pass therethrough while restricting a flow of liquids. In this manner the baffle and the Gortex film act to maintain liquid on one side of the breather while allowing fluids to freely pass therethrough.

These and other aspects of the present invention will become more readily apparent by reference to the following detailed description of the embodiments as shown in the drawings.

BRIEF DESCRIPTION OF THE DRAWINGS

FIG. 1 is an exploded view of the breather of the present invention;

FIG. 2a is a partially assembled view of the breather of the present invention;

FIG. 2b is a partially assembled view of the present invention in cross-section of 2a; and FIG. 3 is a side view of a fully assembled breather of the present invention.

DETAILED DESCRIPTION OF THE PREFERRED EMBODIMENT

The preferred embodiment of the present invention as shown in exploded view in FIG. 1 and partially assembled condition in FIG. 2A, includes a cylindrical member 10 having three portions. The first portion 12 having a thread 14 formed on the outmost surface thereof. The first portion includes a bore 16 extending axially therethrough. A second portion 18 of cylindrical member 10 includes a hexagonally shaped structure 20 defined on the outermost surface. A bore 22 passes axially therethrough and features a diameter larger than bore 16, thereby defining a radially extending annular wall 24. A third portion 26 extends axially from the second portion 18 and includes a bore 28 extending axially therethrough. Bore 28 features a diameter larger than bore 22, thereby forming a radially extending annular wall 30. The bore 22 defines a chamber in which baffle 32 may be placed. Baffle 32 includes a radially extending annular portion 34 which is continuously connected with an inwardly extending radial portion 38 having at least one opening 40 therein. Inwardly extending portion 38 includes an axially extending portion 42 which extends radially proximate opening 40 defined on inwardly extending radial portion 38. Baffle 32 functions to impede the flow of any fluid entering bore 16 which includes a pressure greater than the pressure present in the immediate atmospheric conditions existing around the outside of breather 10. The radially extending annular portion 34 of baffle 32 is placed in supporting relation with annular wall 30. An O-ring is located in bore 28 on an uppermost surface of annular portion 34 of baffle 32. A Gortex film 46 is then disposed thereon and a wire mesh 48 applied thereover. Radially inwardly turned lip 50 is rolled over to trap baffle 32, O-ring 44, Gortex film 46, and wire mesh 48 to provide a rigid structural assembly. Cap 52 featuring deformable tabs 54 is then installed over third portion 26 to provide a loose fitting shield permitting passage of gases therethrough.

One skilled in the art will readily recognize that certain specific details shown in the foregoing specification and drawings are exemplary in nature and subject to modification without departing from the teachings of the disclosure. Various modifications of the invention discussed in the foregoing description will become apparent to those skilled in the art. All such variations that basically rely on the teachings through which the invention has advanced the art are properly considered within the spirit and scope of the invention.

I claim:

1. A venting mechanism comprising:
an axially extending cylindrical member defining three axially displaced continuously connected portions:

a first portion having a thread defined on an outermost surface thereof and having a first bore defined therein;

a second portion having a hexagonally shaped structure defined on an outermost surface thereof and having a second bore defined therein;

said first bore and said second bore intersecting to define a first annular surface between said first and said second bores;

a third portion having a third bore defined therein which defines an annular surface between said second and said third bores;

said second portion defining a chamber including a baffle disposed therein;

said baffle having a first radially extending annular portion continuously connected with a first axially extending cylindrical portion continuously connected with a second radially extending portion defining at least one opening therein;

said second radially extending portion including an axially extending portion connected to a third radially extending portion which extends radially proximate said opening defined on said second radially extending portion;

said first radially extending annular portion of said baffle disposed in supporting relation with said annular surface between said second and said third bores of said third portion of said tubular member;

said third portion including an axially extending cylindrical portion defining said third bore including an O-ring disposed on an outermost surface of said first radially extending portion of said baffle;

a film which allows gases to pass therethrough while restricting flow of liquids extending continuously across said third bore and disposed in contact with said O-ring;

a wire mesh extending continuously across said third bore and disposed in contact with said film; and said third portion having a radially inwardly turned lip which at least partially distorts said O-ring and provides retention for said film, mesh and O-ring in said third bore.

* * * * *